United States Patent
Drews et al.

(10) Patent No.: US 8,330,237 B2
(45) Date of Patent: Dec. 11, 2012

(54) CORROSION-RESISTANT MEMS COMPONENT AND METHOD FOR THE PRODUCTION THEREOF

(75) Inventors: Jürgen Drews, Frankfurt (DE); Karl-Ernst Ehwald, Frankfurt (DE); Katrin Schulz, Frankfurt (DE)

(73) Assignee: IHP GmbH—Innovations for High Performance Microelectronics, Frankfurt (DE)

( * ) Notice: Subject to any disclaimer, the term of this patent is extended or adjusted under 35 U.S.C. 154(b) by 209 days.

(21) Appl. No.: 12/452,426

(22) PCT Filed: Jun. 27, 2008

(86) PCT No.: PCT/EP2008/058316
§ 371 (c)(1),
(2), (4) Date: Mar. 19, 2010

(87) PCT Pub. No.: WO2009/003958
PCT Pub. Date: Jan. 8, 2009

(65) Prior Publication Data
US 2010/0207216 A1    Aug. 19, 2010

(30) Foreign Application Priority Data
Jun. 29, 2007   (DE) .......................... 10 2007 031 128

(51) Int. Cl.
*H01L 29/84* (2006.01)
(52) U.S. Cl. ......... 257/415; 257/E29.324; 257/E21.001; 257/E21.211
(58) Field of Classification Search .................. 257/415, 257/E29.324, E21.001, E21.211
See application file for complete search history.

(56) References Cited

U.S. PATENT DOCUMENTS

| | | | |
|---|---|---|---|
| 2001/0045122 A1 | 11/2001 | Ehwald et al. | 73/54.23 |
| 2003/0062193 A1 | 4/2003 | Thaysen et al. | 174/255 |
| 2003/0124462 A1 | 7/2003 | Miller | 430/311 |
| 2008/0028837 A1* | 2/2008 | Djakov et al. | 73/54.38 |
| 2009/0014819 A1 | 1/2009 | Loeffler et al. | 257/415 |

FOREIGN PATENT DOCUMENTS

| | | |
|---|---|---|
| DE | 100 27 684 | 6/2001 |
| DE | 10 2005 016 243 | 9/2006 |
| DE | 10 2005 055 083 | 5/2007 |
| WO | WO 2005/054814 | 6/2005 |

OTHER PUBLICATIONS

Statement of Relevance for DE 10 2005 055 083.

* cited by examiner

*Primary Examiner* — Telly Green
(74) *Attorney, Agent, or Firm* — Ware, Fressola, Van Der Sluys & Adolphson LLP

(57) ABSTRACT

An MEMS component including a monolithically integrated electronic component with a multi-plane conductor track layer stack which is arranged on a substrate and into which is integrated a cantilevered elastically movable metallic actuator which is arranged in the multi-plane conductor track layer stack at the level of a conductor track plane and is connected by via contacts to conductor track planes which are arranged thereabove or therebeneath and which apart from an opening in the region of the actuator are separated from the conductor track plane of the actuator by a respective intermediate plane insulator layer, wherein the actuator is formed from a metallically conductive layer or layer combination which is resistant to corrosive liquids or gases and which contains titanium nitride or consists of titanium nitride.

11 Claims, 4 Drawing Sheets

CORROSION-RESISTANT MEMS COMPONENT AND METHOD FOR THE PRODUCTION THEREOF

CROSS REFERENCE TO RELATED APPLICATIONS

This application is for entry into the U.S. national phase under §371 for International Application No. PCT/EP2008/058316 having an international filing date of Jun. 27, 2008, and from which priority is claimed under all applicable sections of Title 35 of the United States Code including, but not limited to, Sections 120, 363 and 365(c), and which in turn claims priority under 35 USC §119 to German Patent Application No. 10 2007 031 128.3 filed on Jun. 29, 2007.

BACKGROUND OF THE INVENTION

1. Technical Field

The invention concerns a microelectromechanical structure (MEMS), in particular a sensor which is capable of operating in corrosive gases or liquids with for example a high salt concentration and which in an especial configuration can be a sensor for a microviscosimeter. The invention further concerns a method for the production of such a structure, such a sensor and in particular a microviscosimeter.

2. Discussion of Related Art

DE 100 27 684 B4 discloses a device and a method for viscosity measurement. The operating principle of the viscosimeter described therein will firstly be briefly discussed hereinafter.

Arranged in a measurement zone on a mechanical stable substrate are two or more conductors which are arranged at a small spacing and of which at least one is connected to a controlled current source or to an HF voltage source. A second conductor, here also referred to as the actuator, is held in entirely or portion-wisely cantilevered relationship within the measurement zone. A force required for elastic flexing thereof is generated by a high frequency field between the actuator and a conductor track region which is arranged beneath same and which is also referred to as the base plate, wherein the frequency of the high frequency field is a multiple higher than the natural resonance frequency of the arrangement.

The position of the actuator which is held in cantilever relationship within the measurement zone can be altered, utilizing the elasticity of its holding arrangement or utilizing its own elasticity, by voltage-dependent or current-dependent electrical or magnetic attraction or repulsion forces. Those forces are modified in respect of time by means of the HF voltage sources or current sources.

The capacitance of the arrangement comprising the actuator, the base plate and a medium filling the space between them is a measurement of the elastic flexing of the actuator by the electrical attraction force of the above-mentioned electrical high frequency field. That capacitance reactively influences the oscillator frequency as it is an integrated component of the LC or ring oscillator generating the high frequency field.

By virtue of a change in the attraction or repulsion forces and by virtue of a change in position of the actuator, which is delayed in dependence on the viscosity of the medium to be investigated, it is possible to draw conclusions about the viscosity of the medium to be investigated, by means of an integrated measurement device. The viscosity of a liquid filling the space between the actuator and the base plate can therefore be determined on the basis of the measurable period of time which is required after the oscillator is switched on for predetermined frequency detuning thereof with respect to its starting frequency.

Structural features of the device known from DE 100 27 684 B4 and the process technology for production thereof are briefly described hereinafter.

The actuator is to compromise a very thin elastic and preferably surface-insulated or passivated material. Passivated aluminum is given as an example. A movable conductor loop of aluminum is produced after manufacture of all active and passive components of an integrated circuit of the viscosimeter, by a procedure whereby, prior to the opening of passivation windows and prior to separation of the sensor chips produced on a wafer, an additional photolithographically structured lacquer mask is applied. By means thereof, the part of the uppermost conductor track plane, which is provided for the movable conductor loop, of the integrated circuit is under-etched by a local isotropic insulator etching process and completely separated from the insulating substrate.

The method known from DE 100 27 684 B4 for the production of the actuator of a microviscosimeter using the uppermost conductor track plane of a conventional multi-plane conductor track system suffers from the disadvantage that the proposed actuator structures used of surface-insulated or passivated aluminum Al are not permanently corrosion-resistant in corrosive media such as a blood plasma.

That problem concerns generally MEMS structures which in operation are exposed to corrosive gases or liquids.

The underlying technical object of the present invention is therefore that of providing an MEMS structure or an MEMS component such as for example a sensor, for instance a microviscosimeter, which is particularly resistant in a corrosive medium and which at the same time can be produced with a conventional backend process. From method points of view the object of the invention is to provide a method for the production of such an MEMS component.

DISCLOSURE OF INVENTION

In accordance with a first aspect of the invention the technical object concerning a device is attained by an MEMS component as set forth in claim 1.

The MEMS component according to the invention includes a monolithically integrated electronic component with a multi-plane conductor track layer stack arranged on a substrate. Integrated in the multi-plane conductor track layer stack is a self-supporting elastically movable metallic actuator which is arranged in the multi-plane conductor track layer stack at the level of a conductor track plane and is connected by via contacts to conductor track planes arranged thereabove or therebelow. Apart from an opening in the region of the actuator the conductor track planes are separated by a respective intermediate plane insulator layer from the conductor track plane of the actuator. The actuator is formed from a metallically conductive, conducting layer or layer combination which is resistant to corrosive liquids. The actuator layer contains titanium nitride or consists of titanium nitride.

The MEMS component according to the invention has the advantage that the material titanium nitride used for the actuator and for the base plate is particularly stable in corrosive media and at the same time is compatible with a conventional backend process for the production of microelectronic circuits. The MEMS structure according to the invention is therefore particularly suitable for use in corrosive gases or liquids such as for example saline solutions or blood plasma or in other liquids which contain such corrosive components. At the same time it can be inexpensively produced with known standard processes.

Usually in microsystem technology, micromechanically operating cantilevers and other actuators are made from monocrystalline silicon or polysilicon. Those materials are not suitable for an MEMS structure such as for example a microviscosimeter at an oscillator operating frequency of some GHz inter alia because of the excessively high layer resistance and for reasons of difficulty in integration of the production process in a standard CMOS procedure.

Corrosion-resistant noble metals such as Au, Ag, Pt and so forth are admittedly used in part in microsystem technology, but they are not readily compatible with a conventional backend process for integrated circuits.

In contrast the MEMS component according to the invention, to implement the actuator, uses a layer containing or consisting of titanium nitride. A conductor track plane only consisting of titanium nitride is not considered for normal circuitry applications because of the higher electrical resistance of titanium nitride in comparison with conventional conductor track materials such as aluminum-copper (AlCu) or copper (Cu). However thin titanium nitride in the thickness range of between 40 and 100 nm fulfils the requirement of being completely compatible with a conventional backend process as it is a component of the conductor track stack typically used in an AlCu backend process.

The MEMS component according to the invention has further advantages which are explained hereinafter.

The use of thin titanium nitride in the above-indicated thickness range, with a layer which is optimized in respect of capacitance and power consumption of an oscillator, already allows elastic flexing of the actuator of some µm at an HF effective voltage of about 1 V. In the specific example of use of a microviscosimeter that degree of flexing is required for sufficiently accurate viscosity measurement.

The elastically suspended actuator arrangement, using titanium nitride, is still mechanically particularly stable after the etching-free operation, for example in relation to the processes for cleaning or resist removal during production of the MEMS component according to the invention.

The configuration of the MEMS component according to the invention in the multi-plane conductor track layer stack of the integrated electronic component makes it possible to adjust a spacing which is optimum for a given application between the elastically movable actuator and the base plate, by the selection of a suitable conductor track plane for the actuator and for the base plate. The spacing is adjustable by the sum of the thicknesses of the intermediate plane insulator layers disposed therebetween.

The MEMS component of the invention can be used in many applications. The MEMS structure, provided in the multi-plane conductor track layer stack, of the MEMS component according to the invention is admittedly particularly suitable for use in an MEMS resonator. That however is not to be interpreted as a restriction. In other embodiments the MEMS structure can be used for technical utilization of other physical effects. It can be employed for example in a thermoelectric measurement method. Thus the actuator layer can be used for example for providing a temperature-dependent electrical resistance. That can be technically used in connection with the measurement of a gas pressure, as is described in DE 10 2005 055 083 A1. The term "actuator layer" or "actuator" is therefore to be interpreted in the context of the present application in such a way that it embraces an actuator of a resonator structure as a preferred embodiment, but is not restricted thereto.

Embodiments by way of example of the MEMS component according to the invention are described hereinafter. The additional features of the embodiments can be combined together to form further configurations, unless they are expressly described in the description as alternatives to each other.

In an embodiment by way of example of the MEMS component according to the invention a corrosion-resistant and metallically conductive base plate forms a counter-electrode of the actuator. The base plate is preferably formed by a conductor track region, covered with titanium nitride, of a conductor track plane of the multi-plane conductor track layer stack, or a highly doped region of the semiconductor substrate.

In an embodiment of the MEMS component of the present invention the actuator is formed by a TiN layer of a thickness of between 40 and 100 nm at the level of the third conductor track plane of a 4-plane conductor track system.

In an embodiment the actuator is fixedly anchored in the intermediate plane insulator layer at the edge of the opening at least two mutually opposite suspension points. In that case it preferably involves a mirror-symmetrical lateral structure having at least two conductor track portions perpendicular to the connecting line between the suspension points, in the proximity of an axis of symmetry of the opening. That geometry of the actuator allows better stretchability of the actuator in the direction of the connecting line between the suspension points. It is thus possible on the one hand to permit sufficient flexing, that is to say a sufficient change in capacitance, in the case of an HF voltage of less than 1V, without having to tolerate uncontrolled initial flexing of the actuator structure as a consequence of mechanical stresses within the thin actuator layer. The flexing effects which are inevitable in the case of strong internal stresses, of parts of that actuator structure perpendicularly to the conductor track plane, with the described structure of this embodiment, lead to a further improvement in the stretchability of the actuator in the direction of the connecting line between the suspension points.

In an alternative embodiment a cantilever which is clamped at one side forms the actuator. Preferably in that case the actuator layer involves internal mechanical stresses which are such that the cantilever is controlledly bent away from the base plate with an increasing spacing from its suspension point. Internal stresses can be specifically and targetedly influenced for example by an actuator comprising a plurality of layers.

In a further embodiment arranged on the conductor track plane of the actuator are conductor track structures which contain the actuator layer as part thereof. In that way it is possible to use further layers of the conductor track structures for optimization of conductivity, while they are selectively removed in the region of the actuator structure. In terms of method technology the removal operation is preferably effected in the same step as etching of the intermediate plane insulator layers, but it is also possible by means of a separate masking step prior to or after structuring of the metal plane in question.

The conductor tracks and the base plate can be formed for example from a Ti/TiN/AlCuTi/TiN layer combination.

Alternatively the base plate can be formed by a highly doped active region, which is optionally covered with metal silicide or titanium nitride, of a semiconductor substrate, on which the multi-plane conductor track layer stack is disposed.

The described advantages of the invention can be used in various application situations. A field of application, which is preferred at the present time, of the MEMS component according to the invention is a microviscosimeter.

In accordance with a second aspect of the invention the object concerning the method is attained by a production method for an MEMS component as set forth in claim 11. The method comprises the following steps:

producing a multi-plane conductor track layer stack to the level of a conductor track plane provided for an actuator, wherein respective conductor track planes comprising a metallically conductive conductor track material are separated by a respective intermediate plane insulator layer;

producing a metallically conductive elastically movable actuator layer which is resistant to corrosive liquids and which contains titanium nitride or consists of titanium nitride, on the conductor track plane provided for same;

producing an opening in the multi-plane conductor track layer stack in the region of the actuator layer by a procedure whereby at least one intermediate plane insulator layer between the actuator and the substrate is removed by selective isotropic wet-chemical etching with an etching agent, preferably in combination with a previously executed RIE process, in such a way that the actuator is in cantilever relationship; and contacting the actuator by producing via contacts with conductor track planes arranged thereover or therebeneath, wherein production of the via contacts is effected prior to or after production of the actuator layer.

Using titanium nitride in the production of the actuator layer makes it possible not only to achieve the structural advantages which were already discussed in connection with the description of the MEMS component in accordance with the first aspect of the invention. From the point of view of method procedure the use of titanium nitride in the actuator layer has the further advantage that etching the actuator free, can be effected by means of a selective isotropic wet-chemical etching step. In that case, it is possible to dispense with the use of a hard mask and instead thereof it is possible to use a suitable more stable resist mask. A hard mask and the removal thereof suffers from the disadvantage that deposit and removal thereof can adversely affect the quality of a passivation layer on the uppermost conductor track plane of the multi-plane conductor track system. That disadvantage is circumvented with the method according to the invention.

The use of titanium nitride further allows the use of highly selective etching agents.

Embodiments of the method in accordance with the second aspect of the present invention are described hereinafter. Here too the additional features of various embodiments can be combined together to form further configurations of the method according to the invention, unless the embodiments in question are described as alternatives to each other.

Preferably production of the opening in the multi-plane conductor track layer stack is effected only after completion of the multi-plane conductor track layer stack to and inclusive of production of a passivation layer of a highest conductor track plane.

The etching agent used to produce the opening in the multi-plane conductor track layer stack in the region of the actuator layer, in an embodiment, advantageously contains ethylene glycol, water, ammonium fluoride and hydrofluoric acid. In an embodiment the etching agent comprises those components in a suitable composition. That etching agent has the advantage that it involves etching of typically used intermediate plane insulator layers of $SiO_x$, SiON or SiN in highly selective fashion to give metals. The desired high selectivity of that etching agent is for example in relation to aluminum, aluminum/copper, titanium, tungsten, and also in relation to titanium nitride and metal alloys such as cobalt silicide, titanium silicide and platinum silicide.

In a further embodiment, in production of the opening, removal of the at least one intermediate plane insulator layer is effected using a photolacquer mask or using a combination of a photolacquer mask with a hard mask. In the latter case the hard mask can be a constituent part of the passivation stack and in contrast to conventional hard masks does not have to be selectively removed again after the etching operation, which is difficult to implement in the backend process. The hard mask is structured by way of the photolacquer mask (with a wet-chemical etching agent or a plasma-chemical procedure). Thereafter the photolacquer mask remains on the hard mask during the etching operation and is removed only thereafter. That reduces the demands in terms of the etching resistance of the hard mask.

In wet-chemical etching of the intermediate plane insulator layers which are used in the backend process and which are typically several micrometers thick, over a photolacquer mask, the etching stability thereof is of particular significance. In an embodiment that is achieved by the use of a combination of lacquer bonding agents for increasing the adhesive strength of the photolacquer. After etching of the at least one intermediate plane insulator layer the photolacquer mask is suitably removed by means of polar solvents. Examples of suitable solvents are acetone and isopropanol or a combination of those solvents.

It is important that in a subsequent drying process for removal of the solvent, a so-called "stiction effect" and thus plastic deformation of the actuator structure is avoided. That is achieved in an embodiment in which the solvent is displaced in a drying process by cyclohexane which is transferred by means of cooling into the solid aggregate state and is removed by way of a freeze drying process. An alternative method is to remove the solvent for removal of the photolacquer mask, by means of liquid carbon dioxide. In an embodiment in that case the carbon dioxide is put into a supercritical state by increasing the temperature to a value above 32° C. and increasing the pressure to a value above 74 bars. After removal of the solvent for removal of the photolacquer mask the carbon dioxide used for that purpose is also removed without the actuator structure being plastically deformed. This alternative embodiment of the drying process also makes it possible to removed the solvent without plastic deformation of the actuator.

BRIEF DESCRIPTION OF THE DRAWINGS

Further embodiments are defined in the appendant claims.
The invention is described hereinafter by means of additional embodiments. In the drawing:

DETAILED DESCRIPTION

Figure 1:
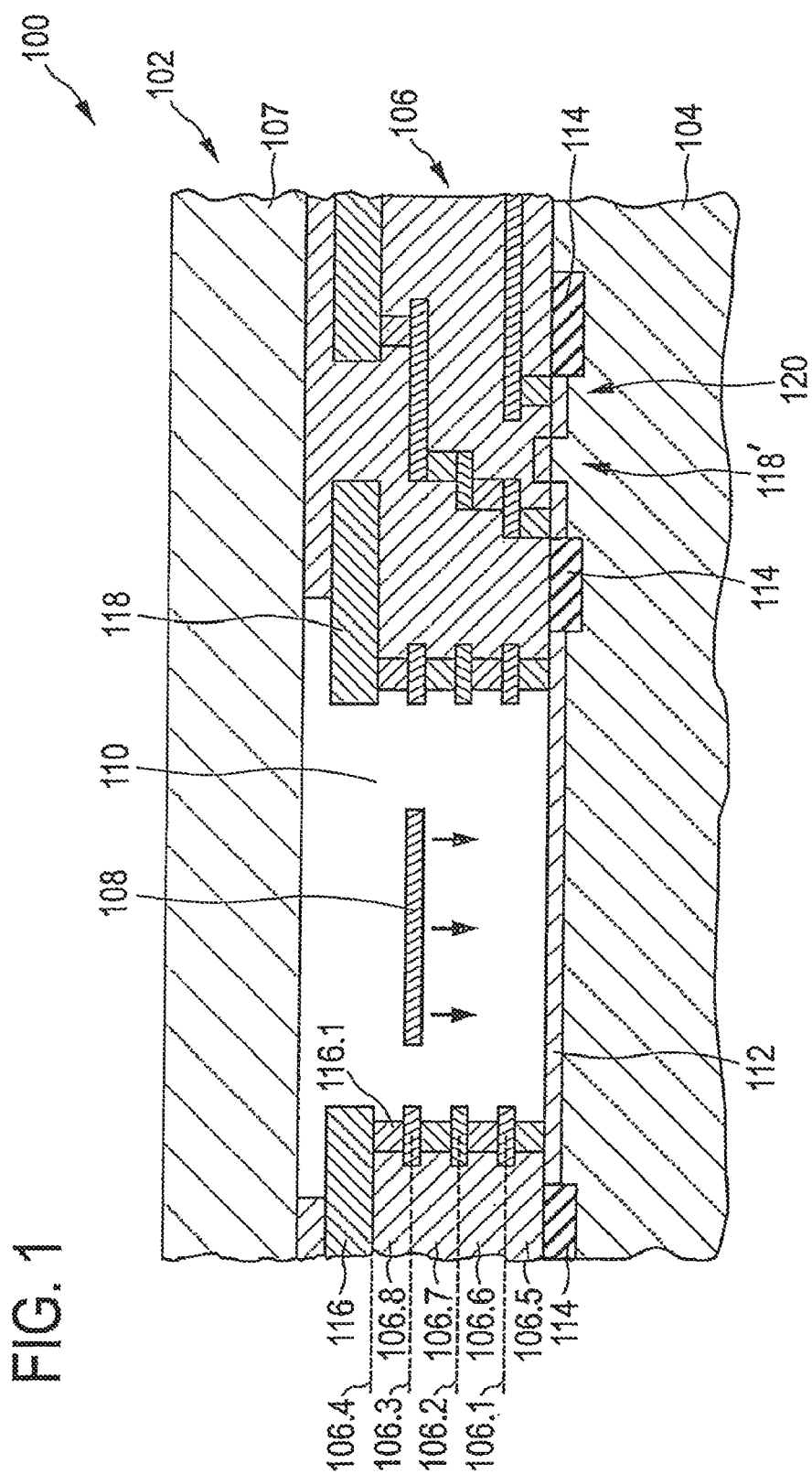
FIG. 1 shows a diagrammatic cross-sectional view of an MEMS component using the example of a microviscosimeter in a first cross-sectional plane.

FIG. 1 shows a simplified cross-sectional view of an MEMS component using the example of an MEMS resonator for a microviscosimeter 100. The example of a microviscosimeter represents a situation of use of the MEMS component of the present invention, which is particularly considered at the present time. It is however not to be interpreted as restricting the invention. The MEMS component can also be used in other use contexts. In particular it is particularly suitable where the MEMS component is exposed to a corrosive medium. A corrosive medium is for example often involved in the detection of climatic ambient parameters (gas pressure, relative humidity, dew point, temperature), in particular in production environments but for example also when measuring air humidity at sea.

The microviscosimeter includes a monolithically integrated electronic component 102 which on a silicon substrate 104 includes a multi-plane conductor track layer stack 106 covered by a semipermeable membrane 107.

An actuator 108 is integrated in the multi-plane conductor track layer stack 106. The actuator is arranged in the multi-plane conductor track layer stack 106 at the level of the third conductor track plane 106.3, calculated from the silicon substrate. The four conductor track planes 106.1 through 106.4 of the multi-plane conductor track layer stack 106 are indicated by broken lines in FIG. 1 at the left-hand edge of the component 102.

Mechanical holding and electrical contacting of the actuator 108 is not shown in the present cross-sectional view. That is described in greater detail with reference to FIG. 2.

The actuator 108 is formed by a titanium nitride layer. Alternatively the actuator can also be formed by a multi-layer structure which for example includes an AlCu core and a TiN sheath. This alternative embodiment is not shown here. The actuator is of a thickness of between 40 and 100 nm and is therefore markedly thinner than a typical conductor track layer.

In the multi-plane conductor track layer stack 106 an opening 110 is formed around the actuator 108. That opening extends from the fourth conductor track plane 106.4 down to the silicon substrate 104. Provided on the silicon substrate in the region of the opening is a siliconized highly n-conductive (n$^+$-) region 112 forming the base plate of the microviscosimeter. The base plate is arranged in an active region defined by flat insulation regions 114. Suitable silicides for forming the base plate 112 are for example cobalt silicide, titanium silicide and platinum silicide. The base plate is connected to external circuit parts by way of contacts 116 and 118 formed by means of conductor track and via structures. Via segments such as for example the via segment 116.1 are disposed, as is known, between the conductor track planes.

The Figure also shows a further active region 118' in the silicon substrate, in which an MOS transistor 120 is arranged. The MOS transistor corresponds in its structure to a usual transistor which can be produced using CMOS technology and is shown in FIG. 1 by way of example, being therefore representative of a suitable active electronic component of an integrated circuit. The MOS transistor 120 can be for example part of an integrated measuring device which otherwise is not shown in greater detail here. The measuring device serves in the microviscosimeter for measuring the period of time until a predetermined frequency detuning is reached after an oscillator is switched on, with respect to a starting frequency—see the description of the mode of operation of the microviscosimeter in DE 100 27 684 B4 in the introductory part of the present patent application.

In another embodiment the measuring device can also be provided on another silicon chip which can be connected to the microviscosimeter. The provision of additional active electronic components on the silicon substrate 104 is therefore not a necessary condition.

The mode of operation of the microviscosimeter 100 in FIG. 1 corresponds to the mode of operation, described in the introductory part here, of the microviscosimeter in DE 100 27 684 B4. Further more detailed description will therefore not be included here. It is to be noted that the spacing of the actuator 108 from the base plate 112 can be altered by arranging the actuator on a lower conductor track plane or by arranging the base plate on one of the conductor track planes.

Figure 2:
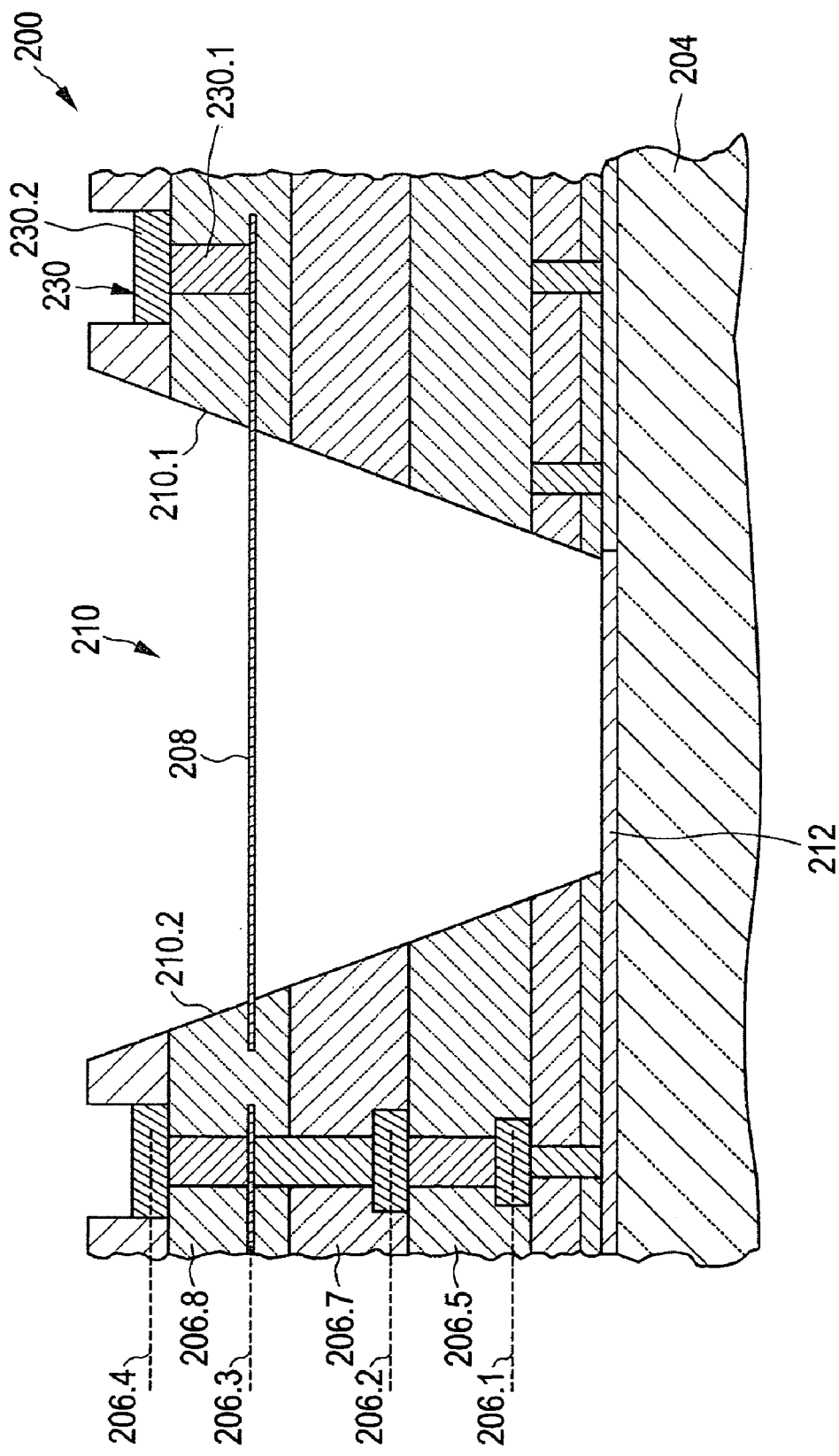
FIG. 2 shows a diagrammatic cross-sectional view of the MEMS component of FIG. 1 in a sectional plane perpendicular to the cross-sectional plane in FIG. 1.

FIG. 2 shows a diagrammatic cross-sectional view of an embodiment of a microviscosimeter 200 in a cross-sectional plane perpendicularly to FIG. 1. The structure of the microviscosimeter 200 in FIG. 2 is the same in essential aspects as the structure of the microviscosimeter 100 in FIG. 1. For that reason mutually corresponding structural features of the two microviscosimeters 100 and 200 are provided with mutually corresponding references which differ only in the first of the three respective digits of the reference in question. The description hereinafter concentrates on the structural features of the microviscosimeter, which can be additionally seen in the sectional plane shown here, in relation to FIG. 1.

The actuator layer 208 of the microviscosimeter 200 is formed by a titanium nitride layer which locally replaces the standard conductor track material, for example aluminum-copper. In another embodiment the complete third conductor track plane is formed by a titanium nitride layer of the thickness of the actuator. In a further preferred embodiment arranged on the conductor track plane of the actuator but outside the lateral region of the actuator are conductor track structures which include the actuator layer as one of a plurality of material layers.

The titanium nitride layer of the actuator 208 is embedded at the longitudinal ends 210.1 and 210.2 of the opening 210, in the layer structure of the multi-plane conductor track layer stack 206. In the present case the actuator is embedded between the intermediate plane insulator layers between the third and fourth conductor track planes 206.3 and 206.4. The intermediate plane insulator layers are formed by means of material layers which are usual in this process. Suitable materials are for example PE-TEOS, SA-USG and SiON.

At the lateral end 210.1 the actuator layer is extended in the multi-plane conductor track layer stack 206 to a contact 203. The contact includes a via structure 230.1 and a conductor track portion 230.2.

Examples of particularly suitable geometrical structures for the actuator 108 and 208 respectively are described hereinafter by means of different embodiments with reference to FIGS. 3 and 4.

Figure 3:
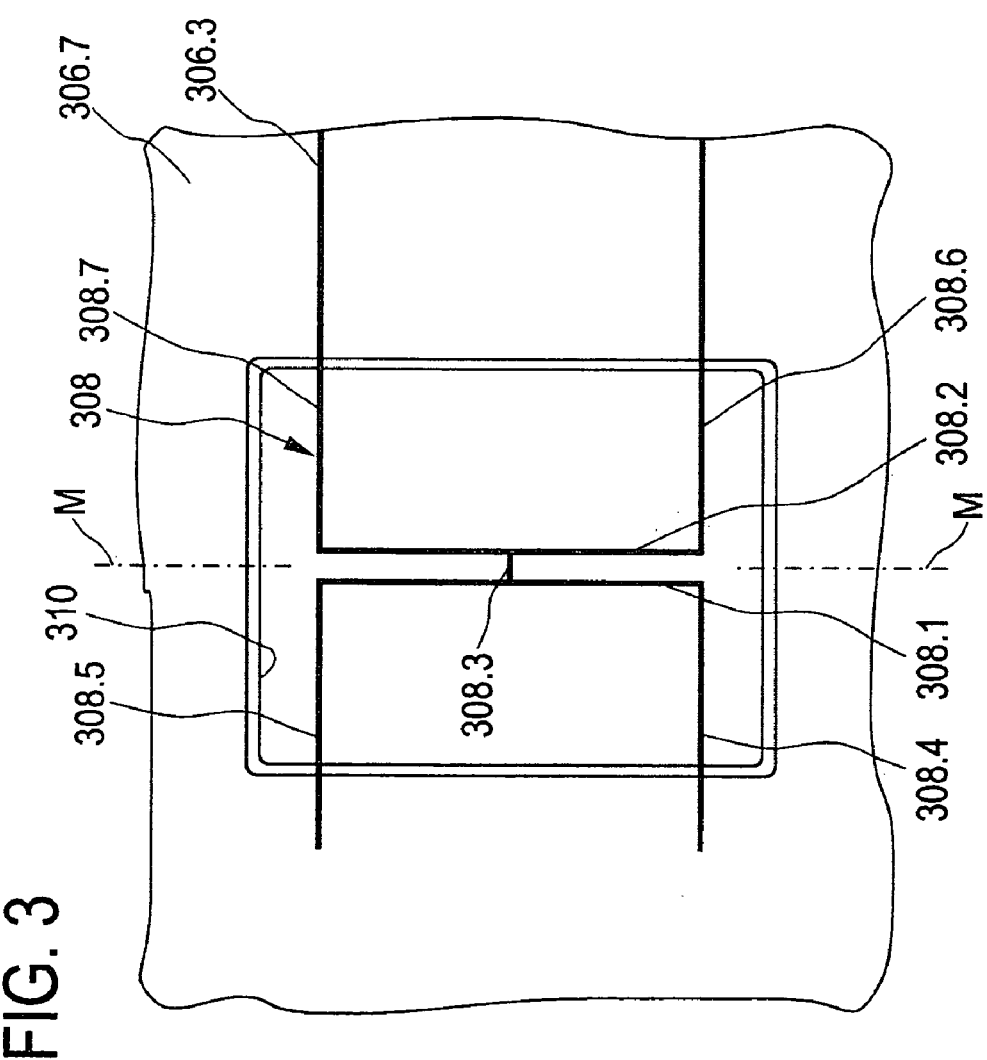
FIG. 3 shows a plan view of an actuator structure in accordance with a further embodiment of the invention.

FIG. 3 shows a plan view of a actuator structure 308 in accordance with a further embodiment of the invention. The actuator 308 is shown in a plan view in which it is possible to see the opening 310 and the extension of the actuator layer 308 in the conductor track plane 306.3, embedded in an intermediate plane insulator 306.7.

The actuator 308 produced from the TiN layer is firmly anchored in the intermediate plane insulator at least two mutually opposite locations, in the present embodiment at the four locations which are in mutually opposite paired relationship, to the edge of the region, which is etched free. More specifically the actuator 308 is embedded at both sides of the opening 310 in the multi-plane conductor track layer stack and anchored therein.

Its geometrical structure is mirror-symmetrical with respect to a center line M of the opening 310. The center line M is only shown in edge areas of the illustrated region, to improve readability in FIG. 3. Two conductor track portions 308.1 and 308.2 of the actuator are arranged parallel to the center line M and in the proximity thereof and are connected together by way of a central limb 308.3. The two conductor track portions 308.1 and 308.2 are therefore at an only small spacing from each other. Those perpendicularly arranged conductor track portions ensure improved stretchability of the actuator in the direction of the connecting line between the suspension points. They are respectively connected thereto by way of further conductor track portions 308.4, 308.5 and 308.6 and 308.7 to give the edge of the opening 310.

The central limb extends perpendicularly to the center line M in the conductor track plane of the actuator 308. Thus it extends at the same time parallel to a notional connecting line between suspension points of the actuator 308 at the edge of the opening 310.

The described arrangement ensures on the one hand, with a sufficiently thin TiN layer (a thickness of between 40 and 100 nm is particularly suitable) adequate flexing with an HF voltage <1 V, while on the other hand preventing uncontrolled flexing of the actuator structure as a consequence of mechanical stresses within the thin TiN layer. The flexing effects, which are inevitable in the case of strong internal stresses, in respect of parts of the described actuator structure in perpendicular relationship to the metal plane or the wafer surface lead to a further improvement in the stretchability of the actuator in the direction of the connecting line between the suspension points, with a suitable geometrical arrangement.

Figure 4:
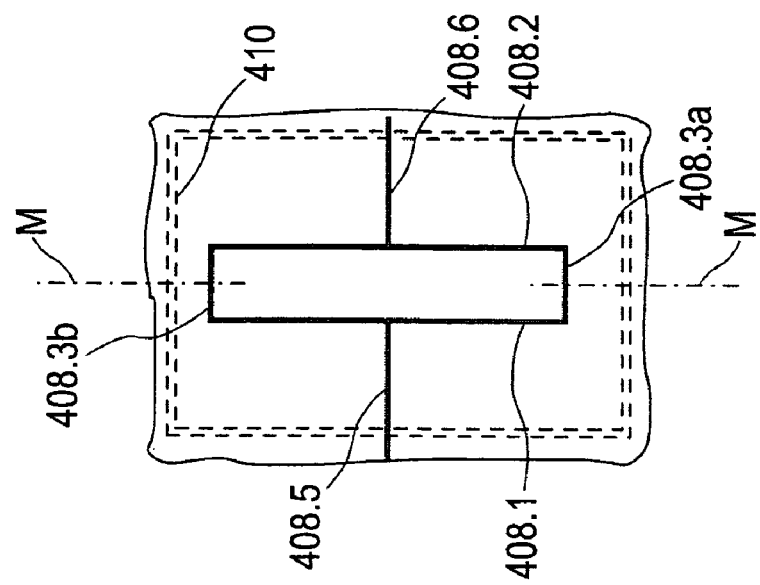
FIG. 4 shows a plan view of a further actuator structure of another embodiment of the invention.

FIG. 4 shows a diagrammatic plan view of a further actuator structure 408 in accordance with another embodiment of the invention. The actuator form 408 shown in FIG. 4 fulfils the same symmetry properties as the actuator structure 308 in FIG. 3. However, instead of a central limb, the actuator structure 408 includes two central limbs 408.3a and 408.3b forming the short sides of a rectangle enclosed by axis-parallel conductor track portions 408.1 and 408.2 and the central limbs. The axis-parallel conductor track portions, unlike the structure shown in FIG. 3, are each extended to the respectively most closely adjacent edge of the opening, only by way of a single conductor track portion 408.5 and 408.6 respectively which engages same perpendicularly and centrally.

Figure 5:
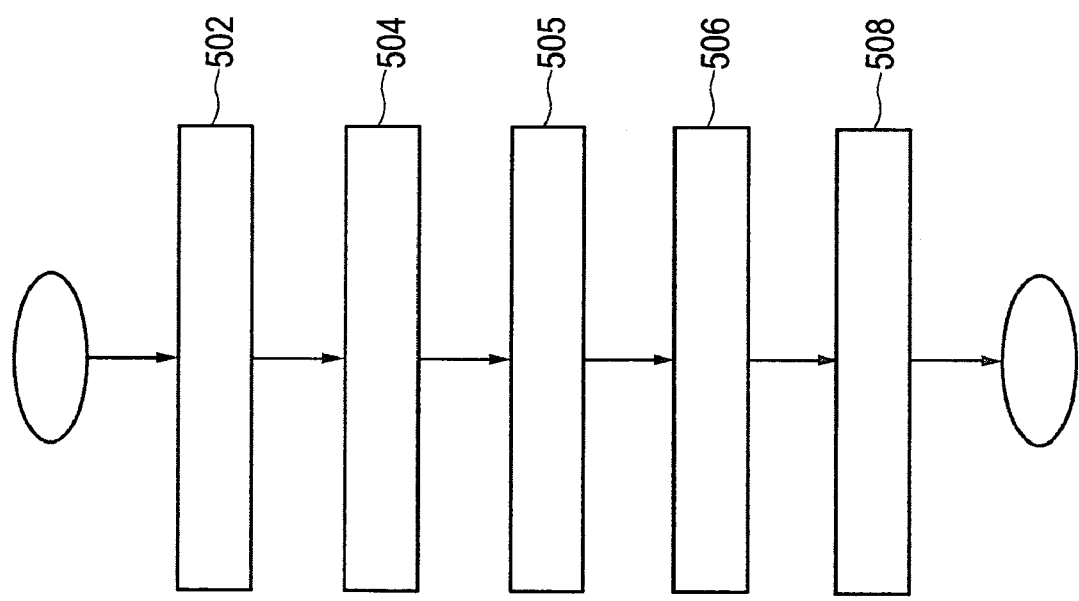
FIG. 5 shows a flow chart of an embodiment of an MEMS component production method.

FIG. 5 shows a flow chart of an embodiment of a production method for a microviscosimeter corresponding to the examples shown in FIGS. 1 through 4.

The method includes the following steps:

Step 502: producing a multi-plane conductor track layer stack to the level of a conductor track plane intended for an actuator, wherein respective conductor track planes of a metallically conductive conductor track material are separated by a respective intermediate plane insulator layer.

Per se known backend processes of CMOS or BiCMOS technology are used for this method step. In the context of depositing the multi-plane conductor track layer stack, the base plate is produced on a desired conductor track plane. Alternatively it is produced prior to production of the conductor track layer stack in an active region on the substrate surface.

Step 504: Producing a metallically conductive, elastically movable actuator layer which at least locally replaces the conductor track material of the conductor track plane in question and which is resistant to corrosive liquids and which contains or consists of titanium nitride.

That TiN layer is suitably arranged between the uppermost standard conductor track plane and the plane therebeneath, and is separated from them by a respective intermediate plane insulator and is connected to adjacent conductor track planes by means of standard vias.

The spacing between the actuator and the base plate can if necessary be reduced or optimized by the TiN layer being arranged between two conductor track planes disposed at a lower level, or, as in the examples in FIGS. 1 and 2, by the spacing between the actuator and the base plate extending over a plurality of conductor track planes.

The actuator produced from the foregoing TiN layer is firmly anchored in the intermediate plane insulator material by subsequent layer deposition at least two opposite locations at the edge of the region which is etched free.

In an embodiment the conductor track plane which contains the actuator does not otherwise have any additional conductor tracks. There is then no need for the deposition of further materials for the additional conductor tracks which, by virtue of the conductivity requirements, generally have to be made from materials other than titanium nitride. As is known titanium nitride does not involve high conductivity.

Typically however the conductor track material is only locally replaced by titanium nitride in the region of the actuator. The layer stack of the conductor track plane is preferably so selected that the layer or layer succession which later forms the actuator is a component part thereof.

Step 505: completing the backend stack to the passivation operation inclusive.

Step 506: producing an opening in the multi-plane conductor track layer stack in the region of the actuator layer by a procedure whereby at least one intermediate plane insulator layer is removed between the actuator and the substrate by selective isotropic wet-chemical etching with an etching agent, in such a way that the actuator is in cantilever relationship.

That purpose is served by using an etching method which isotropically removes the insulator layers used in the backend process, in highly selective relationship with respect to the metals used in the backend process such as aluminum, tungsten and titanium nitride and with respect to the metal silicide forming the base plate (cobalt silicide, titanium silicide, platinum silicide).

In wet-chemical etching of the plurality of μm-thick intermediate plane insulator layers used in the backend process, by way of a structured photolacquer (photolacquer mask), the etching stability thereof is of particular significance. That is achieved by using a special etch-resistant photolacquer and by a combination of gaseous and liquid bonding agents for increasing the adhesive strength of the photolacquer.

For that purpose, prior to the lacquer coating operation, liquid lacquer bonding agent is applied and then heat-treated. Immediately prior to the lacquer coating operation, so-called priming is also effected, by means of a primer. After the coating with photolacquer, the thickness of which can be varied between 4 and 6 μm, further heat treatment is effected for the entire system. Exposure to light and development of the photolacquer is suitably matched to its thickness. Then, some nanometers of the photolacquer are removed in an oxygen plasma to clean the window in the photolacquer and precisely match the lacquer edge to the insulator in a finishing procedure.

Preferably wet-chemical etching agents are used for removal of the insulator layers by way of the photolacquer mask, for example an etching agent comprising ethylene glycol, water, aluminum fluoride and hydrofluoric acid. By means of that etching agent, it is possible for all insulator layers of the CMOS or BiCMOS backend to be removed by way of the photolacquer mask in highly selective relationship with respect to TiN or other metals and metal alloys of which the actuator structure of the microviscosimeter can consist.

The etching agent then stops highly selectively on the metal silicide of the counter-electrode (base plate).

In an alternative embodiment the etching duration is so selected that residues of the insulator layers are not removed beneath the actuator, but are retained. It is possible in that way to prevent contact with the base plate and thus a short-circuit from occurring in operation of the microviscosimeter at maximum deflection of the actuator.

After the termination of the etching process flushing is effected with deionized water to remove the etching agent. Thereafter the photolacquer mask is removed in solvents, for example in acetone.

To avoid a so-called "stiction effect" and thus plastic deformation of the actuator structure in the subsequent drying process, it is necessary to prevent the actuator structure from being severely bent in the direction of the counter-electrode due to the surface tension of the solvent volume which is reduced in the drying process, in the etched structures.

One method is to displace the solvent for removal of the photolacquer mask by another solvent which has a low freezing point (for example cyclohexane). The cyclohexane is converted into the solid aggregate state by means of cooling and removed by way of a freeze drying process.

A further method is to remove the solvent for removal of the photolacquer mask by means of liquid carbon dioxide, putting the carbon dioxide into a supercritical state by increasing the temperature above 32° C. and the pressure above 74 bars and removing it, without the actuator structure being plastically deformed.

The method further includes (step 508), contacting of the actuator by production of via contacts with conductor track planes arranged thereabove or therebeneath, wherein production of the via contacts is suitably carried out in the context of the backend process prior to or after production of the actuator layer.

What is claimed is:

1. An MEMS component including a monolithically integrated electronic component with a multi-plane conductor track layer stack which is arranged on a semiconductor substrate and into which is integrated a cantilevered elastically movable metallic actuator which is arranged in the multi-plane conductor track layer stack at the level of a conductor track plane and is connected by via contacts to conductor track planes which are arranged thereabove or therebeneath and which apart from an opening in the region of the actuator are separated from the conductor track plane of the actuator by a respective intermediate plane insulator layer, wherein the actuator is formed from a metallically conductive layer or layer combination which is resistant to corrosive liquids or gases and which contains titanium nitride or consists of titanium nitride, and comprising a corrosion-resistant and metallically conductive base plate forming a counter-electrode of the actuator, wherein the base plate is formed by a conductor track region, covered with titanium nitride, of a conductor track plane or formed by an active region of the semiconductor substrate, that is covered with a metal silicide or titanium nitride.

2. The MEMS component as set forth in claim 1 in which the actuator is formed by a TiN layer of a thickness of between 40 nm and 100 nm.

3. The MEMS component as set forth in claim 1 in which the actuator is firmly anchored in the intermediate plane insulator layer at at least two mutually opposite suspension points at the edge of the opening and has a mirror-symmetrical lateral structure with at least two conductor track portions which are perpendicular to the connecting line between the suspension points in the proximity of an axis of symmetry of the opening.

4. The MEMS component as set forth in claim 1 in which the actuator is formed by a cantilever which is clamped at one side, wherein the actuator layer contains internal mechanical stresses which are such that the cantilever is bent away from the base plate at the non-clamped lateral end.

5. The MEMS component as set forth in claim 1 in which an intermediate plane insulator residue is arranged on a portion of the base plate as a stopper for excessive deflection of the actuator.

6. The MEMS component as set forth in claim 1 in which conductor track structures containing the actuator layer as one of a plurality of metal layers are arranged on the conductor track plane of the actuator but outside the lateral region of the actuator.

7. A microviscosimeter having an MEMS component as set forth in claim 1.

8. The MEMS component as set forth in claim 1, wherein the actuator is formed by a layer of the conductor track plane containing or consisting of titanium nitride.

9. The MEMS component as set forth in claim 8, wherein the layer locally replaces the standard conductor track material, preferably aluminum-copper.

10. The MEMS component as set forth in claim 8, wherein the complete conductor track plane of the actuator is formed by the layer.

11. The MEMS component as set forth in claim 1, wherein the actuator is formed by a multi-layer structure which includes an AlCu core and a TiN sheath.

* * * * *